US011867557B2

United States Patent
Ni et al.

(10) Patent No.: US 11,867,557 B2
(45) Date of Patent: Jan. 9, 2024

(54) AUTOMATIC AMBIENT LIGHT CANCELLATION METHOD FOR OPTICAL FRONT-END METHODS AND APPARATUS

(71) Applicant: Analog Devices International Unlimited Company, Limerick (IE)

(72) Inventors: Jinhua Ni, Shanghai (CN); Hui Shen, Shanghai (CN)

(73) Assignee: ANALOG DEVICES INTERNATIONAL UNLIMITED COMPANY, Limerick (IE)

( * ) Notice: Subject to any disclaimer, the term of this patent is extended or adjusted under 35 U.S.C. 154(b) by 0 days.

(21) Appl. No.: 17/412,598

(22) Filed: Aug. 26, 2021

(65) Prior Publication Data

US 2023/0030688 A1 Feb. 2, 2023

Related U.S. Application Data

(63) Continuation of application No. PCT/CN2021/109646, filed on Jul. 30, 2021.

(51) Int. Cl.
*G01J 1/44* (2006.01)

(52) U.S. Cl.
CPC .......... *G01J 1/44* (2013.01); *G01J 2001/444* (2013.01)

(58) Field of Classification Search
CPC ................................ G01J 1/44; G01J 2001/444
See application file for complete search history.

(56) References Cited

U.S. PATENT DOCUMENTS

| 8,847,578 | B2 | 9/2014 | Venkataraman et al. |
| 9,900,018 | B1 * | 2/2018 | Chen ................. H03M 1/08 |
| 10,145,736 | B2 | 12/2018 | Ahmed et al. |
| 2005/0045807 | A1 * | 3/2005 | Sakaguchi ............. G01J 1/18 |
| | | | 250/214 R |
| 2011/0114842 | A1 * | 5/2011 | Ji ......................... G01S 7/4868 |
| | | | 250/340 |
| 2013/0021018 | A1 * | 1/2013 | Venkataraman ...... H03M 3/494 |
| | | | 324/123 R |
| 2018/0156660 | A1 * | 6/2018 | Turgeon .................. A61B 5/681 |
| 2019/0257688 | A1 * | 8/2019 | Balamurugan ........ G01J 1/0252 |
| 2020/0037901 | A1 * | 2/2020 | Trattler ................ A61B 5/02416 |

(Continued)

FOREIGN PATENT DOCUMENTS

DE 102017127963 A1 * 5/2019

OTHER PUBLICATIONS

International Search Report and Written Opinion in PCT/EP2022/071124, dated Nov. 23, 2022, 12 pages.

(Continued)

*Primary Examiner* — Jennifer D Bennett
(74) *Attorney, Agent, or Firm* — ArentFox Schiff LLP

(57) ABSTRACT

Automatic ambient light cancellation for an optical front end. The present disclosure includes a coarse loop and fine loop in a feedback circuit configured to cancel out currents generated by detection of ambient light. An optical front end comprises a single-ended photo-diode connected to a transimpedance amplifier (TIA) followed by a buffer stage to generate differential output. A feedback loop controls a current digital to analog converter (iDAC) which is used to cancel out undesired current (e.g., from ambient light). This results in the TIA from saturating and maintain good signal quality with greater sensitivity.

19 Claims, 9 Drawing Sheets

(56) References Cited

U.S. PATENT DOCUMENTS

2020/0375483 A1* 12/2020 Bremer ................ A61B 5/7225
2021/0000357 A1* 1/2021 Li .......................... A61B 5/681
2021/0123801 A1* 4/2021 Liu ...................... A61B 5/7203
2021/0270965 A1* 9/2021 Liu ....................... G01S 7/4814

OTHER PUBLICATIONS

Xu et al., "A 665 [mu]W Silicon Photomultiplier-Based NIRS/EEG/EIT Monitoring ASIC for Wearable Functional Brain Imaging," IEEE Transactions on Biomedical Circuits and Systems, Dec. 2018, vol. 12, No. 6, pp. 1267-1277.

* cited by examiner

AUTOMATIC AMBIENT LIGHT CANCELLATION METHOD FOR OPTICAL FRONT-END METHODS AND APPARATUS

CROSS-REFERENCE TO RELATED APPLICATIONS

This application is a continuation of and claims the benefit of priority under 35 U.S.C. § 120 and 35 U.S.C. § 363 to International Application No. PCT/CN2021/109646 entitled, "AUTOMATIC AMBIENT LIGHT CANCELLATION METHOD FOR OPTICAL FRONT-END METHODS AND APPARATUS" filed on Jul. 30, 2021, which is hereby incorporated by reference in its entirety.

FIELD OF THE DISCLOSURE

Embodiments of the invention are directed, in general, to electronic systems and, more specifically, to a low noise, low power front end for a pulsed input system and methods using same.

BACKGROUND

Oximeters are photoelectric devices which measure the oxygen saturation of blood. Historically, these devices were first used in clinical laboratories on samples of blood taken from patients. In recent years, non-invasive oximeters have been developed and are now widely used in intensive care units to monitor critically ill patients and in operating rooms to monitor patients under anesthesia. Early non-invasive devices relied on dialization of the vascular bed in, for example, the patient's ear lobe to obtain a pool of arterial blood upon which to perform the saturation measurement.

More recently, non-invasive devices known as "pulse oximeters" have been developed which rely on the patient's pulse to produce a changing amount of arterial blood in, for example, the patient's finger or other selected extremity. Pulse oximeters for home use are small, lightweight monitors that painlessly attach to a fingertip to monitor the amount of oxygen carried in the body. An oxygen level of greater than 95% is generally considered to be a normal oxygen level. An oxygen level of 92% or less (at sea level) suggests a low blood oxygen.

Pulse oximetry is a noninvasive method for monitoring a person's oxygen saturation ($SO_2$). Though its reading of $SpO_2$ (peripheral oxygen saturation) is not always identical to the more desirable reading of SaO2 (arterial oxygen saturation) from arterial blood gas analysis, the two are correlated well enough that the safe, convenient, noninvasive, inexpensive pulse oximetry method is valuable for measuring oxygen saturation in clinical use.

Pulse oximeters measure oxygen saturation by (1) passing light of two more selected wavelengths, e.g., a "red" wavelength and an "IR" wavelength, through the patient's extremity, (2) detecting the time-varying light intensity transmitted through the extremity for each of the wavelengths, and (3) calculating oxygen saturation values for the patient's blood using the: Lambert-Beers transmittance law and the detected transmitted light intensities at the selected wavelengths.

Less commonly, reflectance pulse oximetry is used as an alternative to transmissive pulse oximetry described above. This method does not require a thin section of the person's body and is therefore well suited to a universal application such as the feet, forehead, and chest, but it also has some limitations. Vasodilation and pooling of venous blood in the head due to compromised venous return to the heart can cause a combination of arterial and venous pulsations in the forehead region and lead to spurious SpO2 results. Such conditions occur while undergoing anesthesia with endotracheal intubation and mechanical ventilation or in patients in the Trendelenburg position.

For people with COPD, asthma, Congestive Heart Failure (CHF) and other conditions, pulse oximetry is a technology used to measure the oxygen level in your blood and your heart rate. Using a clip to a patient's fingertip, a finger pulse oximeter is equipped with technology to detect changes in your blood oxygen level.

In its most common (transmissive) application mode, a sensor device is placed on a thin part of the patient's body, usually a fingertip or earlobe, or in the case of an infant, across a foot. The device passes two wavelengths of light through the body part to a photodetector. It measures the changing absorbance at each of the wavelengths, allowing it to determine the absorbances due to the pulsing arterial blood alone, excluding venous blood, skin, bone, muscle, fat, and (in most cases) nail polish.

A plethysmograph (PPG) detector is a device for measuring biological events within body tissue. Using a plethysmograph (PPG) detector, and other devices for detecting biological events, operate by measuring changes in transmission or diffuse reflectance from the body tissue or subject under active illumination.

The radiation used for measuring plethysmograph (PPG) signals can span wavelengths from blue to infrared. In classic applications, light emitting diodes (LEDs) of two colors—often 660 nm and 940 nm—are used for measuring blood oxygen saturation. These devices are in large volume production and are readily available. In yet another application, a simple single-color LED—say at 940 nm—may be used to measure heart rate by measuring the periodic variation in a return signal. In some cases, a green LED is used to pick up variation in absorption caused by blood flow on the wrist.

Plethysmograph (PPG) signals are generated by measuring the changes in the transmission or diffuse reflectance of body tissue under active illumination by LED of a particular wavelength. The beating of the heart changes both the mechanical dimensions of the arteries and also blood volume in those arteries. These effects lead to variation in the received light intensity. A typical plethysmograph (PPG) signal makes a signal estimate required to measure parameters such as blood oxygen.

There is developing interest to measure plethysmograph (PPG) signals continuously by incorporating plethysmograph (PPG) sensors/systems in devices that can be attached to a subject, for example, wrist band, watch, in-the-ear buds, etc. In such applications, these devices have to function with very low power and every photon emitted from the LED is precious as it is a drain on a battery. Furthermore, space constraints force the use of small photodiodes to collect diffuse light coming from the tissue. As a result, the signal is small and any reduction in noise of the system can be immediately applied to conserve battery power and increase the time to recharge or replace batteries.

Thus, much attention has been paid to reduce the noise of the receiver systems and noise in the LED drive circuits. Many noise reduction techniques for LED drivers and receivers require extra power. To make matters worse, many visible light LEDs themselves exhibit fairly large "1/f" noise in the generated light. This noise is a result of both 1/f noise in the LED driver as well as the physical mechanisms in the LED, such as the thermal fluctuations and the generation-recombination noise.

Since a heart beats at a relatively low frequency in the range of 0.5-5 Hz (30 to 300 beats per minute), this low frequency noise essentially limits the ability to measure the plethysmograph (PPG) signal. This becomes even more crucial for blood oxygen saturation (SpO2) systems where accurate determinations of both AC and DC components of the plethysmograph (PPG) signal must be made.

A survey of all commercially available PPG systems have $f_D$<0.01. Accordingly, the inventors perceive a need in the art for PPG system that permits reduction of noise in plethysmograph (PPG) signals captured by such systems. Additionally, there is a need for other vital sign monitors, such as, ECG, Biopotential, etc. to be incorporated into wearable devices.

Biopotential measurement is can be used in modern medical procedures. For example, biopotentials can be used for electrocardiogram (ECG), electroencephalogram (EEG), electromyography (EMG), etc.

ECG lead systems are used to obtain biopotential signals containing information indicative of the electrical activity associated with the heart and pulmonary system. To obtain biopotential signals, ECG electrodes are applied to the skin of a patient in various locations and coupled to an ECG device, e.g., an "ECG monitor" or "ECG telemetry." Placement of the electrodes is dependent on the information sought by the clinician.

The placement of the ECG electrodes on the patient has been established by medical protocols. The most common protocols require the placement of the electrodes in a three-lead, a five-lead, or a twelve-lead configuration. A three-lead configuration requires the placement of three electrodes; one electrode adjacent each clavicle bone (RA, LA) on the upper chest and a third electrode adjacent the patient's lower left abdomen (LL). A five-lead configuration requires the placement of the three electrodes in the three-lead configuration with the addition of a fourth electrode adjacent the sternum (Va) and a fifth electrode on the patient's lower right abdomen (RL). A twelve-lead configuration requires the placement of ten electrodes on the patient's body.

Four electrodes, which represent the patient's limbs, include the left arm electrode (LA lead), the right arm electrode (RA lead), the left leg electrode (LL lead), and the right leg electrode (RL lead). Six chest electrodes (V1-V6 leads) are placed on the patient's chest at various locations near the heart. Three standard limb leads are constructed from measurements between the right arm and left arm (Lead I), the right arm and the left leg (Lead II) and the left arm to left leg (Lead III). Other conventional lead configurations include a 14 leads system that incorporated additional leads located on a back surface.

An ECG lead set typically includes an array of three, five, or twelve leads as determined by the intended clinical protocol. Each individual lead wire includes, at a patient end thereof (e.g., distal end), an ECG lead wire connector configured to operably couple the lead wire to an electrode pad affixed to the body of a patient. At the opposite (e.g., proximal) end, the individual lead wires are gathered into a common coupler that is configured to operably couple the array of lead wires to an ECG device.

Leads sets are typically provided with a generous length of lead wire sufficient to reach from the patient to the ECG device. In some instances, however, the lead wire may fall short, in which case a lead wire extension cable having appropriate distal and proximal couplers may be employed. In some instances, the lead wire coupler of an ECG lead set and/or ECG lead extension may be incompatible with an available ECG device, in which case an ECG adapter may be employed that facilitates operable coupling of the otherwise-incompatible physical and/or electrical characteristics of the disparate couplers.

There is a demonstrated need in the art for a wearable device with the capacity to monitor a plurality of vital signs. The inventors of the present disclosure have recognized that an impediment to implementation is noise, and more specifically, background. As such, the inventors contemplate the cancellation of signals generated by ambient light in a dynamic environment.

This overview is intended to provide an overview of subject matter of the present patent application. It is not intended to provide an exclusive or exhaustive explanation of the invention. Further limitations and disadvantages of conventional and traditional approaches will become apparent to one of skill in the art, through comparison of such systems with some aspects of the present invention as set forth in the remainder of the present application with reference to the drawings.

SUMMARY OF THE DISCLOSURE

Automatic ambient light cancellation for an optical front end. The present disclosure includes a coarse loop and fine loop in a feedback circuit configured to cancel out currents generated by detection of ambient light. An optical front end comprises a single-ended photo-diode connected to a transimpedance amplifier (TIA) followed by a buffer stage to generate differential output. A feedback loop controls a current digital to analog converter (iDAC) which is used to cancel out undesired current (e.g., from ambient light). This results in the TIA from saturating and maintain good signal quality with greater sensitivity.

According to one aspect of the present disclosure, an apparatus and/or method for mitigating signals from ambient light in an optical front end comprises a differential amplifier having a first input and a second input and an output, a photodetector in electrical communication with the first input of the differential amplifier, a current source in electrical communication with the first input of the differential amplifier, and a voltage source in electrical communication with the second input of the differential amplifier, wherein the current source is configured to produce current which is substantially equal and opposite to a current produced by the photodetector.

According to anyone of the preceding or proceeding aspects of the present disclosure, an apparatus and/or method for mitigating signals from ambient light in an optical front end further comprises a buffer amplifier having an input and output, the input in electrical communication with the output of the differential amplifier.

According to anyone of the preceding or proceeding aspects of the present disclosure, an apparatus and/or method for mitigating signals from ambient light in an optical front end further comprises an analog to digital converter (ADC) configured to sample the output of the buffer amplifier.

According to anyone of the preceding or proceeding aspects of the present disclosure, an apparatus and/or method for mitigating signals from ambient light in an optical front end further comprises logic configured to control a current produced by the current source.

According to anyone of the preceding or proceeding aspects of the present disclosure, an apparatus and/or method for mitigating signals from ambient light in an optical front end, wherein the current is based on at least on the sample from the ADC.

According to anyone of the preceding or proceeding aspects of the present disclosure, an apparatus and/or method for mitigating signals from ambient light in an optical front end further comprises a comparator.

According to anyone of the preceding or proceeding aspects of the present disclosure, an apparatus and/or method for mitigating signals from ambient light in an optical front end further comprises a successive approximation register (SAR).

According to anyone of the preceding or proceeding aspects of the present disclosure, an apparatus and/or method for mitigating signals from ambient light in an optical front end, wherein the current source is a current digital to analog converter (IDAC).

According to anyone of the preceding or proceeding aspects of the present disclosure, an apparatus and/or method for mitigating signals from ambient light in an optical front end, wherein the logic to control the current is based on information from at least one of IDAC, SAR and comparator.

According to anyone of the preceding or proceeding aspects of the present disclosure, an apparatus and/or method for mitigating signals from ambient light in an optical front end further comprises a feedback resistor in electrical communication with the input and output of the difference amplifier.

According to anyone of the preceding or proceeding aspects of the present disclosure, an apparatus and/or method for mitigating signals from ambient light in an optical front end, wherein the differential amplifier is a transimpedance amplifier (TIA).

According to anyone of the preceding or proceeding aspects of the present disclosure, an apparatus and/or method for mitigating signals from ambient light in an optical front end further comprises a voltage source to reverse bias the photodetector.

According to anyone of the preceding or proceeding aspects of the present disclosure, an apparatus and/or method for mitigating signals from ambient light in an optical front end further comprises wherein the photodetector is a single-ended photodiode.

According to anyone of the preceding or proceeding aspects of the present disclosure, an apparatus and/or method for mitigating signals from ambient light in an optical front end further comprises receiving a first current from a sensor indicative of a measured light, producing a first voltage by passing the first current through a feedback resistor, comparing, at a differential amplifier having an output, the first voltage with a reference voltage, producing a second current from a current source, and canceling at least some of the first current using the second current, wherein the current source is configured to produce the second current which is substantially equal and opposite to a current produced by the sensor.

According to anyone of the preceding or proceeding aspects of the present disclosure, an apparatus and/or method for mitigating signals from ambient light in an optical front end further comprises comparing, at a comparator, whether the output of the differential output is above a predetermine threshold.

According to anyone of the preceding or proceeding aspects of the present disclosure, an apparatus and/or method for mitigating signals from ambient light in an optical front end further comprises sampling the output of the differential amplifier.

According to anyone of the preceding or proceeding aspects of the present disclosure, an apparatus and/or method for mitigating signals from ambient light in an optical front end, wherein the sampling is performed by an analog to digital converter (ADC).

According to anyone of the preceding or proceeding aspects of the present disclosure, an apparatus and/or method for mitigating signals from ambient light in an optical front end further comprises controller the current source using the sampled output, at least in part.

According to anyone of the preceding or proceeding aspects of the present disclosure, an apparatus and/or method for mitigating signals from ambient light in an optical front end, wherein the current source is an IDAC.

The drawings show exemplary optical front ends and configurations. Variations of these circuits, for example, changing the positions of, adding, or removing certain elements from the circuits are not beyond the scope of the present invention. The illustrated circuits, configurations, and complementary devices are intended to be complementary to the support found in the detailed description.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

For a fuller understanding of the nature and advantages of the present invention, reference is made to the following detailed description of preferred embodiments and in connection with the accompanying drawings, in which.

DETAILED DESCRIPTION

Figure 1:
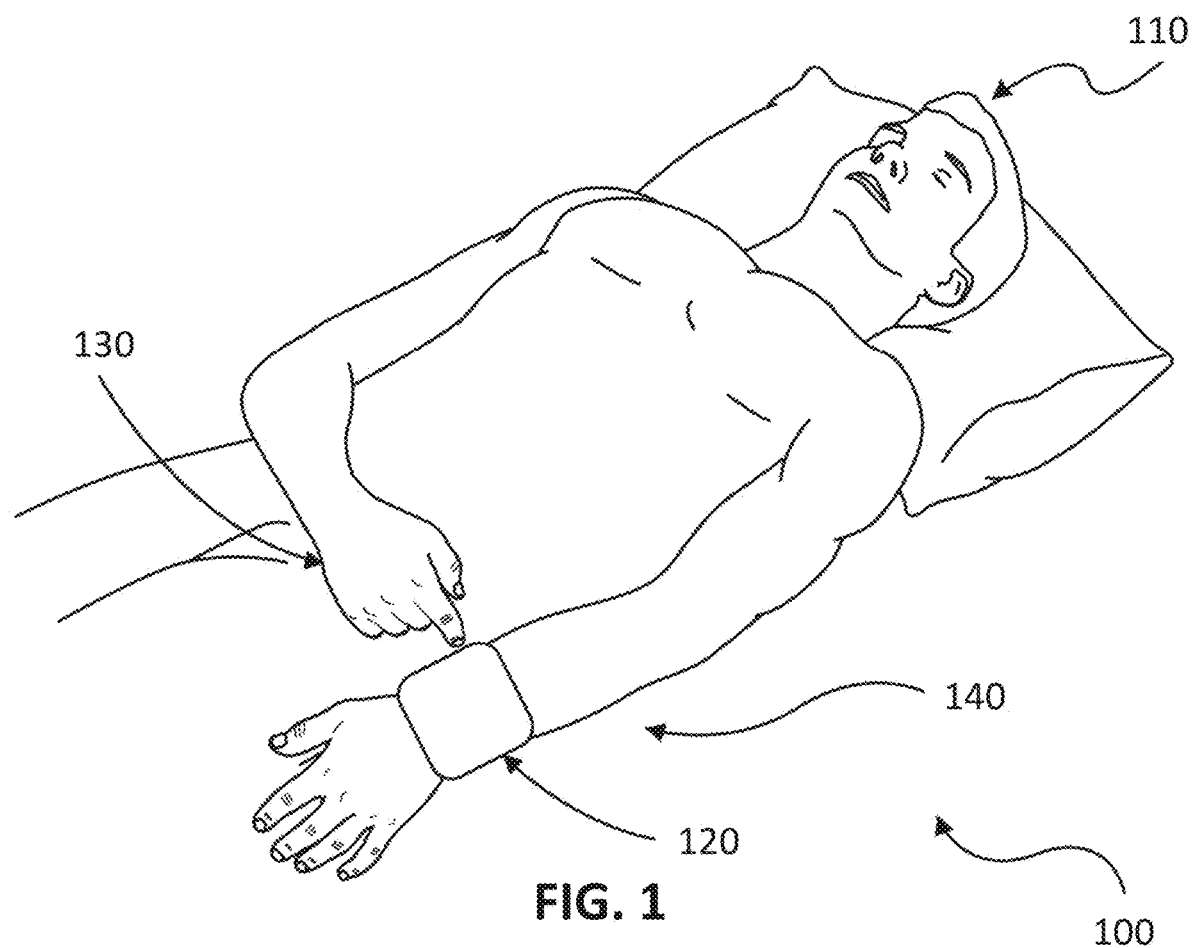
FIG. 1 depicts an exemplary wearable vital sign monitor (VSM), in accordance with some embodiments of the disclosure provided herein.

Various types of electronic devices, such as heart rate monitors and peripheral capillary oxygen saturation (SpO2) monitors, perform functions that require both the emission and detection of light. For example, heart rate monitors may emit light (using, e.g., light-emitting diodes (LEDs)) in the direction of the human body and may detect the light that has reflected back toward the monitor. In such electronic devices, reflected light may be detected using photodiodes, which produce current as a function of the intensity of detected light. The photodiodes, however, detect ambient light in addition to reflected light generated by the electronic devices. The electronic devices attempt to cancel ambient light to the extent possible.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

Pulse-oximetry is a non-invasive method that may be used to monitor the saturation of a patient's hemoglobin. Pulse-oximetry typically utilizes a pair of small light-emitting diodes (LEDs) facing a photodiode through a translucent part of the patient's body, usually a fingertip or an earlobe. One LED is red, with wavelength of 660 nm, and the other is infrared, 905, 910, or 940 nm. Absorption at these wavelengths differs significantly between oxyhemoglobin and its deoxygenated form; therefore, the oxy/deoxyhemoglobin ratio can be calculated from the ratio of the absorption of the red and infrared light. The monitored signal bounces in time with the heart beat because the arterial blood vessels expand and contract with each heartbeat. By examining only the varying part of the absorption spectrum (essentially, subtracting minimum absorption from peak absorption), a monitor can ignore other tissues or nail polish, and discern only the absorption caused by arterial blood.

In measurements systems such as for pulse-oximetry, the desired signal has a very small amplitude that rides on a large ambient offset signal. In pulsed input measurement systems, such as for oximetry, the front end transimpedance amplifiers or gain amplifiers need to have a large bandwidth in order to support the pulsing input signals. The equivalent noise bandwidth of the front end is larger because of the large bandwidth for settling, even though the signal bandwidth of interest is much smaller. The front end gain is usually restricted to avoid saturation of the front end due to the large offset signal in comparison to the signal of interest.

In practice, it is desirable to have a high front end gain without running the risk of saturation. This could be provided at a lower consumptive power while achieving a higher signal to noise ratio (SNR).

FIG. 1 depicts an exemplary wearable vital sign monitor (VSM) 100 comprising plethysmograph (PPG) and electrocardiogram (ECG or EKG) measurements, in accordance with some embodiments of the disclosure provided herein. In one embodiment, a wearable PPG/ECG device 120 is disclosed. Wearable PPG/ECG device 120 is implemented based on subsequent discussion and embodiments, at least in part, using a single analog front end (AFE).

In practice, user 110 creates a biopotential using arm 130 opposite of arm 140 whereon the wearable PPG/ECG device 120 is disposed. Wearable PPG/ECG device 120 also includes PPG measuring device. This is disclosed in greater detail in application Ser. No. 14/500,129 entitled, "LOW FREQUENCY NOISE IMPROVEMENT IN PLETHYSMOGRAPHY MEASUREMENT SYSTEMS," which hereby incorporated by reference in its entirety.

In some embodiments, VSM is used to determine at least one of PPG (Photoplethysmography), ECG/EKG (Electrocardiogram), Bio-Z (Bio-Impedance), HRM (Heart Rate Monitor), HRV (Heart Rate Variability), SPO2 (Saturation level of Pulse Oxygen), BIA (Body Impedance Analysis), Hydration analysis, CNIBP (Cuff-less Non-Invasive Blood Pressure) and PWV (Pulse Wave Velocity).

Pulse wave velocity (PWV) is the velocity at which the arterial pulse propagates through the circulatory system. PWV is used clinically as a measure of arterial stiffness. It is easy to measure invasively and non-invasively in humans, is highly reproducible, has a strong correlation with cardiovascular events and all-cause mortality and an indicator of target organ damage and a useful additional test in the investigation of hypertension. Additionally, high pulse wave velocity (PWV) has also been associated with poor lung function.

A heart rate monitor (HRM) is a personal monitoring device that allows one to measure/display heart rate in real time or record the heart rate for later study. It is largely used to gather heart rate data while performing various types of physical exercise. Measuring electrical heart information is referred to as Electrocardiography (ECG or EKG).

Medical heart rate monitoring used in hospitals is usually wired and usually multiple sensors are used. Portable medical units are referred to as a Holter monitor. Consumer heart rate monitors are designed for everyday use and do not use wires to connect.

Electrocardiography is the process of producing an electrocardiogram (ECG or EKG). It is a graph of voltage versus time of the electrical activity of the heart using electrodes placed on the skin. These electrodes detect the small electrical changes that are a consequence of cardiac muscle depolarization followed by repolarization during each cardiac cycle (heartbeat). Changes in the normal ECG pattern occur in numerous cardiac abnormalities, including cardiac rhythm disturbances (such as atrial fibrillation and ventricular tachycardia), inadequate coronary artery blood flow (such as myocardial ischemia and myocardial infarction), and electrolyte disturbances (such as hypokalemia and hyperkalemia).

Heart rate variability (HRV) is the physiological phenomenon of variation in the time interval between heartbeats. It is measured by the variation in the beat-to-beat interval. Other terms used include: "cycle length variability", "R-R variability" (where R is a point corresponding to the peak of the QRS complex of the ECG wave; and RR is the interval between successive Rs), and "heart period variability."

Methods used to detect beats include: ECG, blood pressure, ballistocardiograms, and the pulse wave signal derived from a photoplethysmograph (PPG). ECG is considered superior because it provides a clear waveform, which makes it easier to exclude heartbeats not originating in the sinoatrial node. The term "NN" is used in place of RR to emphasize the fact that the processed beats are "normal" beats.

Hydration analysis comprises estimating the amount of water in a subject. In extreme cases of low hydration, oral rehydration therapy (ORT) may be applied. ORT is a type of fluid replacement used to prevent and treat dehydration due to activity, but especially due to diarrhea. It involves drinking water with modest amounts of sugar and salts, specifically sodium and potassium.

The current blood pressure (BP) measurement devices are mostly built on the principle of auscultation, oscillometry or tonometry, all of which use an inflatable cuff to occlude or unload the artery. The need of a cuff in these devices limits the further reduction in size and power consumption, and restricts the frequency and ease of their usage. In one or more embodiments, the present disclosure proposes a cuffless and noninvasive technique for measuring BP by pulse transit time.

Figure 2:
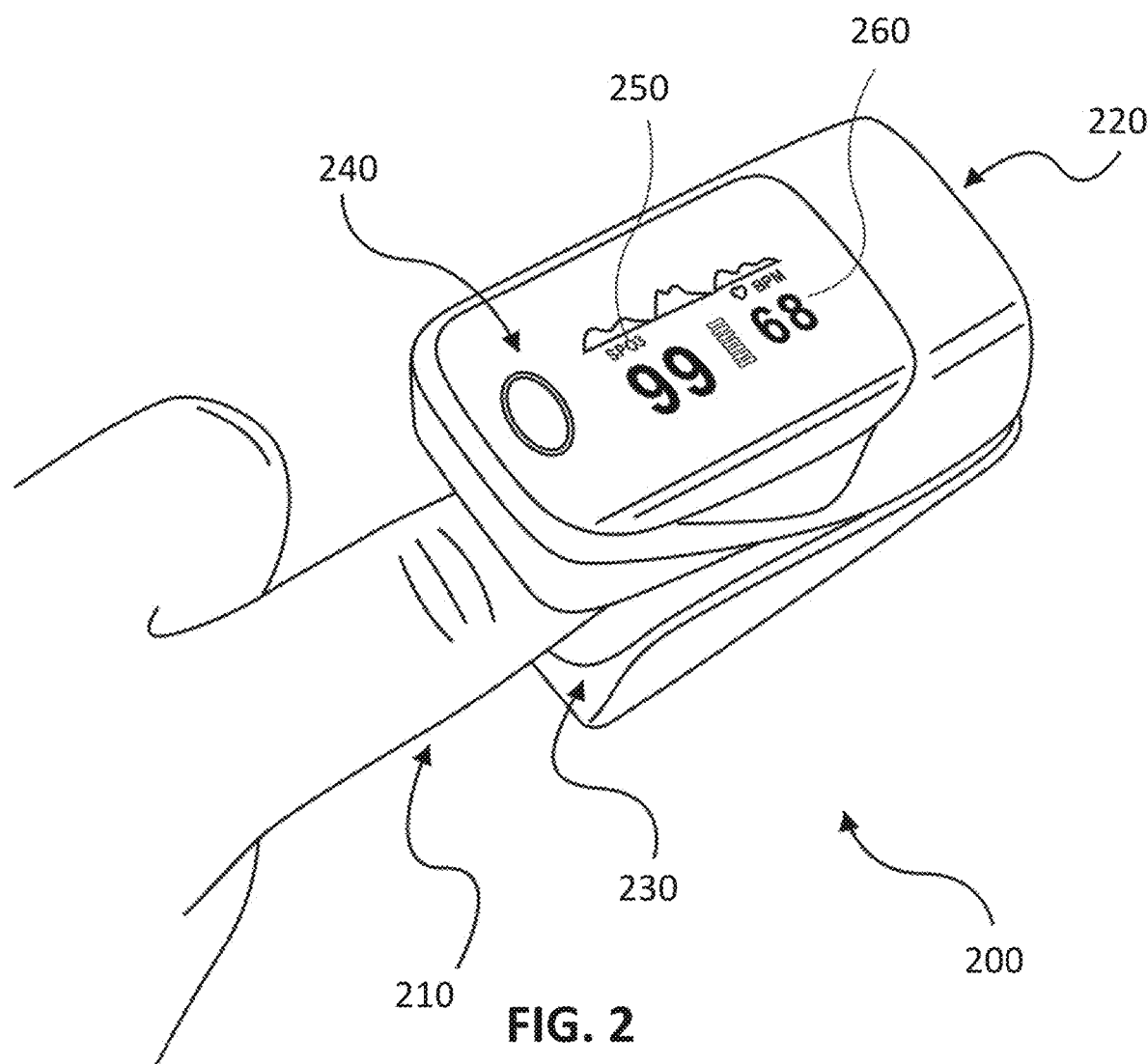
FIG. 2 shows an exemplary pulse oximeter device, in accordance with others embodiments of the disclosure provided herein.

FIG. 2 shows an exemplary pulse oximeter device 200, in accordance with others embodiments of the disclosure provided herein. Pulse oximeter device 200 comprises body 220, function button 240, $SpO_2$ display 250, PR display 260, and finger orifice 230.

Body 220 is constructed in a spring-loaded clothespin fashion. It allows the orifice 230 to securely but safely clamp onto a patient's finger 210. Depending on embodiment/model, function button 240 can be used for on-off power, cycling through modes, cycling through displays and/or checking battery power levels, any of which are not beyond the scope of the current disclosure.

$SpO_2$ display 250 outputs current blood oxygen saturation level as a percentage (unitless). Blood oxygen saturation level ($SpO_2$) is a measure of the amount of oxygen carried in the hemoglobin. $SpO_2$ is expressed as a percentage of the maximum amount of oxygen that hemoglobin in the blood can carry. Since hemoglobin accounts for over 90% of oxygen in blood, $SpO_2$ also measures the amount of oxygen in blood. PR display 260 outputs current pulse rate in units of beats per minute (bpm).

Figure 3:
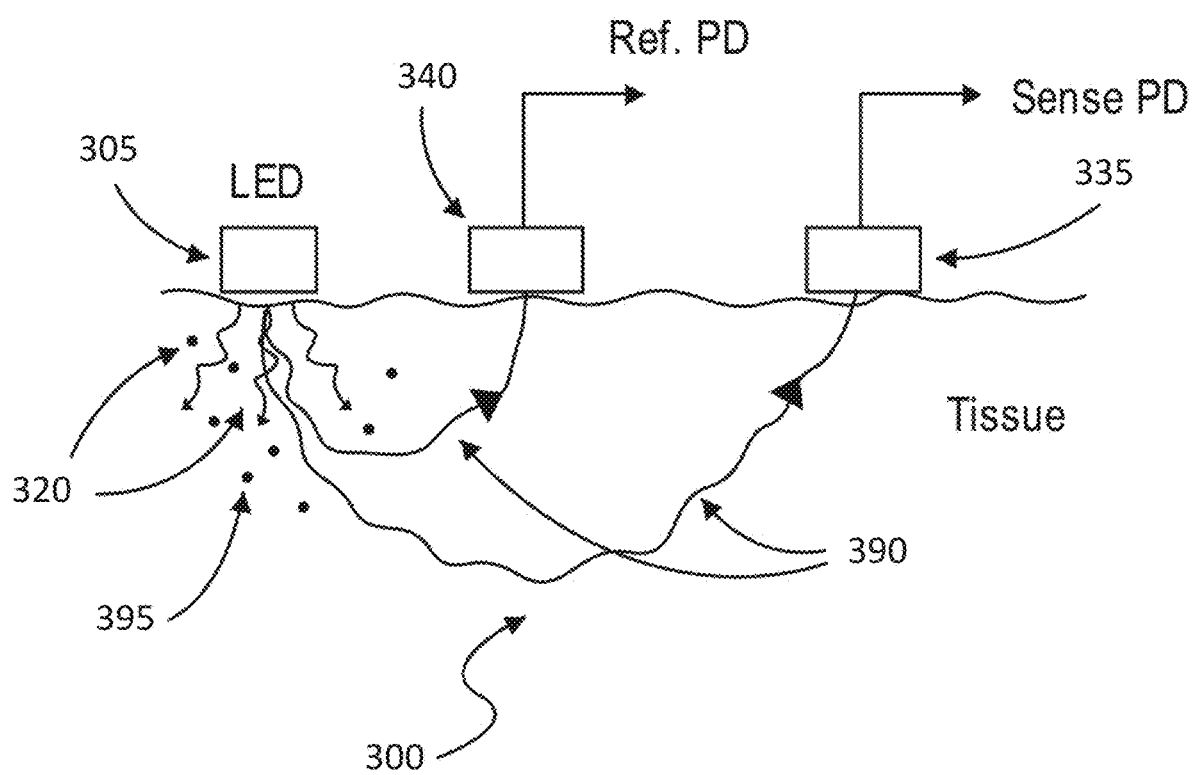
FIG. 3 illustrates an exemplary pulse oximeter in operation, in accordance with others embodiments of the disclosure provided herein.

FIG. 3 illustrates an exemplary pulse oximeter 300 in operation, in accordance with others embodiments of the disclosure provided herein. Exemplary pulse oximeter 300 comprises light emitting diode (LED) 305, sense detector 335, and reference detector 340. One skilled in the art will appreciate that some circuit elements have been omitted but that the principle remains the same as one or more of the previous embodiments.

In practice, light emitting diode (LED) 305 produces light 320 which in turn get scattered off of a predetermined chemical, e.g., $SpO_2$, within the tissue of a subject (patient). Subsequently scatter light 390 gets detected by either reference detector 340 or sense detector 335, depending on scattering trajectory and mean-free-path. This is a function of the light wavelength and chemical interaction which is known in the art.

In one or more embodiments, a separate photodiode may be deployed to act as reference channel to eliminate low frequency variations in the LED's output due to temperature and supply variations. Since a heart beats at roughly 1 Hz, this low-frequency elimination of LED's variation as well as any variation in gains allows one to reach high SNR even with noisy power supplies that generally add lots of noise and systematic variations at low frequencies.

In yet another embodiment associated with FIG. 3, two photodiodes can be used with one closer to the LED designated as the reference PD while the one further away acting as signal PD. In this case, even the variation in the LED's light coupling to the tissue becomes common mode and are eliminated. This will allow more precise measurement of the tissue scattering and absorption compounded with ambient light cancellation which will now be discussed in greater detail.

Figure 4:
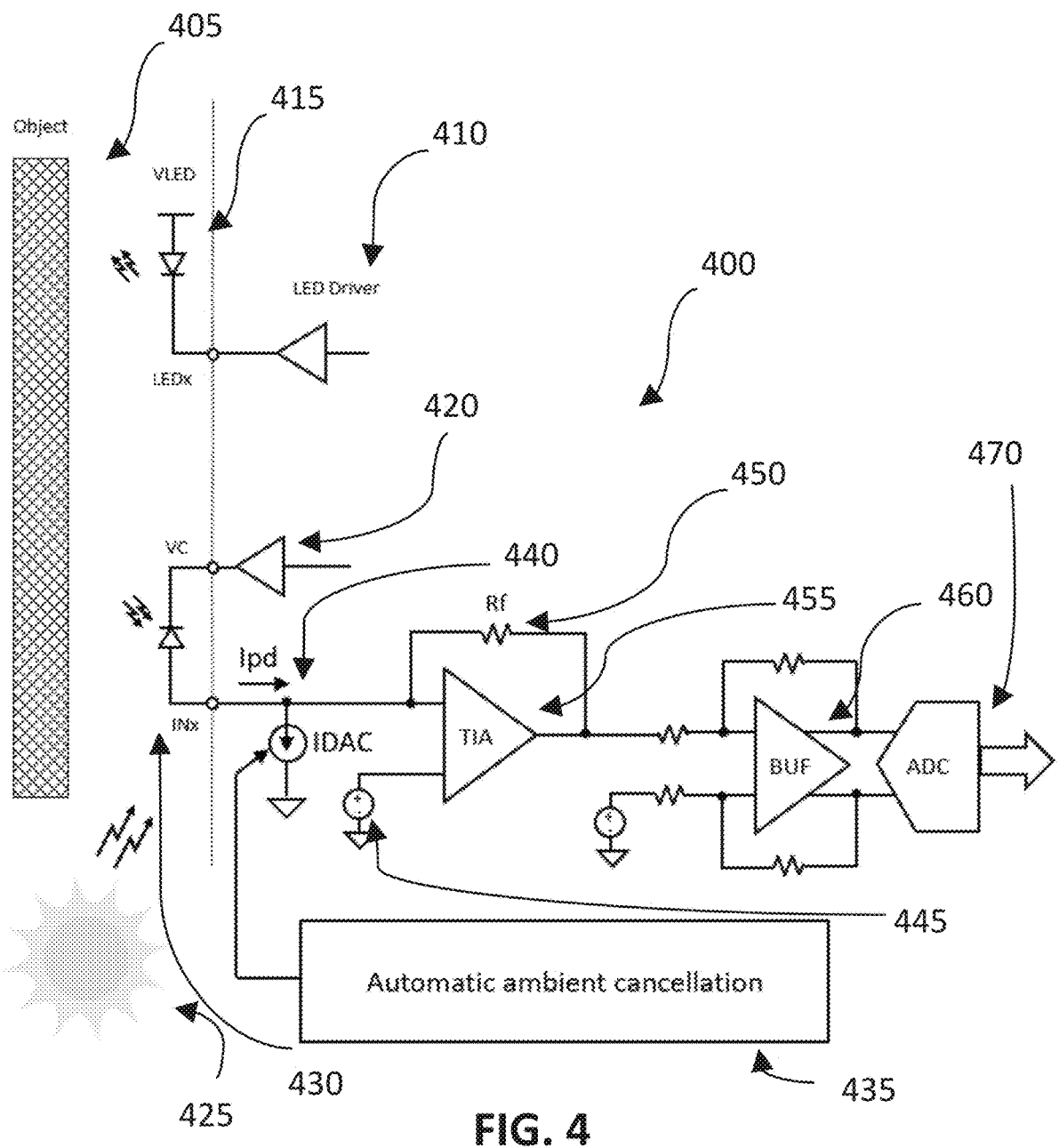
FIG. 4 depicts an exemplary schematic of an exemplary optical front end, in accordance with others embodiments of the disclosure provided herein.

FIG. 4 depicts an exemplary schematic of an exemplary optical front end 400, in accordance with others embodiments of the disclosure provided herein. Optical front end 400 comprises light emitting diode (LED) driver 410, VLED 415, bias amp 420, photodetector 430, automatic ambient cancellation module 435, IDAC 440, feedback resister 450, transimpedance amplifier (TIA) 455, buffer stage 460, analog to digital converter 470, and reference voltage supply 445.

In one or more embodiments, the present disclosure provides an automatic ambient cancellation method and apparatus for optical front end. In practice, the optical front end 400 has a single-ended photo-diode 430 connected to the TIA 445 input, followed by a buffer stage 460 to generate the differential outputs and then drive the ADC 470. The photo-diode 430 current will include the reflected light off an object 405 from the transmitter and the ambient light from the environment.

The ambient light will cause interference to the reflected signal and even saturate the TIA 445 output when it is larger than the TIA 445 linear range. A current DAC (IDAC) 440 circuit is added at the TIA 445 input to cancel the ambient light, such that the TIA input current only contains the compensated light signal and will maintain good signal quality. An automatic ambient cancellation loop including a coarse loop and a fine loop will control the IDAC 440 output. The coarse loop will compare the TIA 445 outputs against the threshold to set the initial DAC control code. The fine loop will use the ADC 470 sample to refresh the DAC control code. This will be discussed in greater detail later in the disclosure.

In one or more embodiments, an initial coarse threshold comes from the positive input bias voltage of the TIA 445, which is the reference voltage supply 545. When the TIA 445 output voltage is equal to this reference voltage, it means the current through the gain resistor Rf 450 is zero. In this case, the ambient current is perfectly cancelled out by the IDAC.

In one or more embodiments, the photo-diode (PD) 430 is reverse biased by amp 420 with its cathode connected to the VC node and with its anode connected to the TIA 455 input, such that the PD 430 current Ipd is always in one direction. As is known in the art, increasing the reverse bias producing greater sensor sensitivity, however at the risk of pushing the TIA 455 out of its linear region and possibly into saturation.

This is exacerbated due to the photo-diode 430 current Ipd including the reflected light from the transmitter (an LED 415) and the ambient light from the environment. In a dynamic environment, such as, found on a wearable device, the background ambient light is ever changing and can easily overwhelm the transmitter signal reflect off an object.

A current DAC circuit (IDAC) 440 is added at the front of the TIA 455 input to cancel the ambient light, such that the TIA 445 input current only contains the compensated light signal and maintain good signal quality. A DAC produces a quantized (discrete step) analog output in response to a binary digital input code. The digital input may be TTL, ECL, CMOS, or LVDS, while the analog output may be either a voltage or a current, as is reflected in the present embodiment.

To generate the output, a reference quantity (either a voltage or a current) is divided into binary and/or linear fractions. Then the digital input drives switches that combine an appropriate number of these fractions to produce the output. The number and size of the fractions reflect the number of possible digital input codes, which is a function of converter resolution or the number of bits (N) in the input code. For N bits, there are $2^N$ possible codes. The analog output of the DAC output is the digital fraction represented as the ratio of the digital input code divided by $2^N$ times the analog reference value.

In general, IDAC 440 receives a digital code from automatic ambient cancellation module 435 and produces a current in opposite direction of Ipd. Specifically, IDAC 440 produces a current equal and opposite to that engendered by ambient, background or otherwise undesirable light. In practice, feedback resister 450 converts the current to a voltage with is passed to the buffer stage, 460. The functionality of automatic ambient cancellation module 435 will now be discussed in greater detail.

Figure 5:
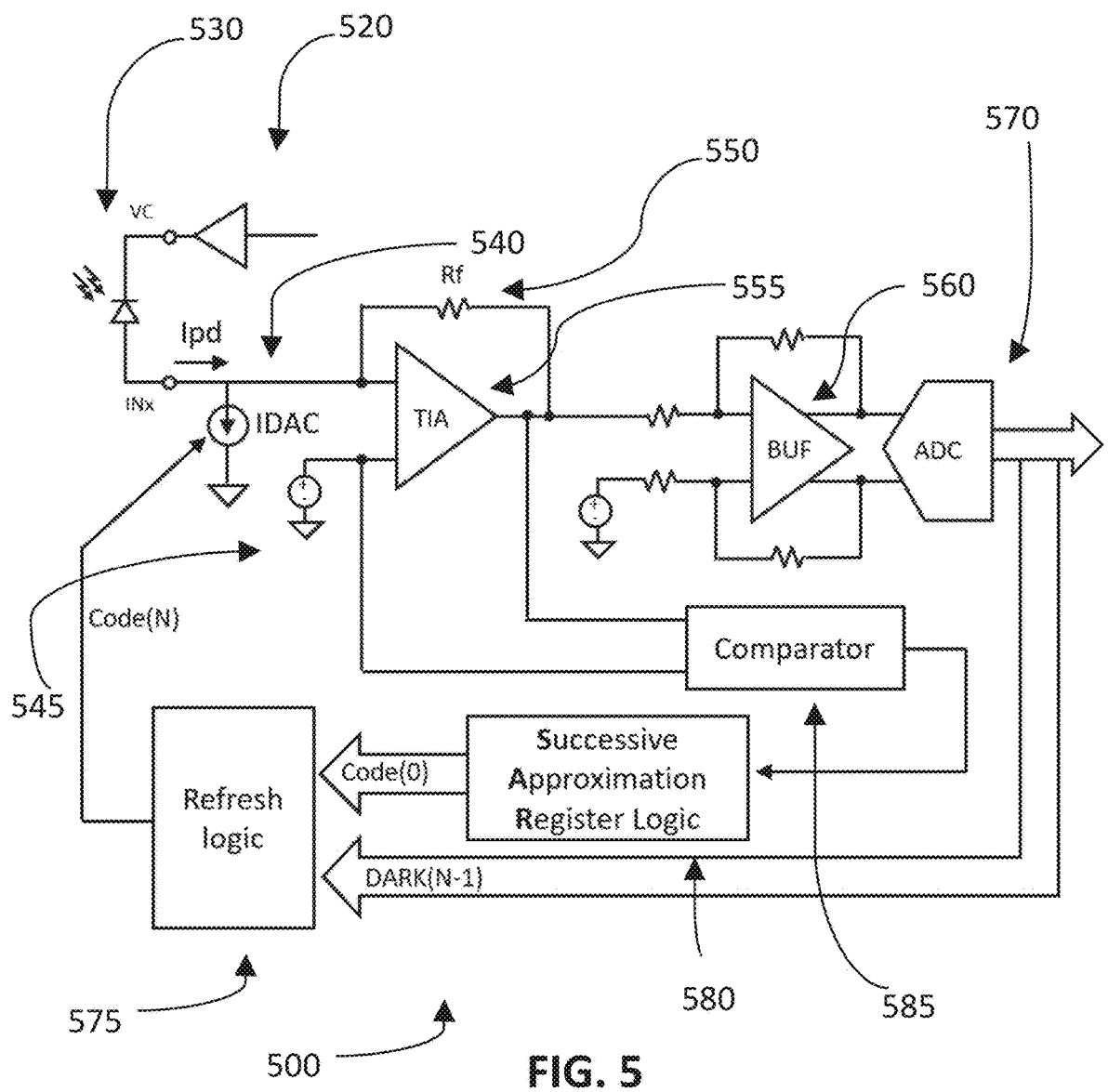
FIG. 5 depicts an alternate exemplary schematic of an exemplary optical front end, in accordance with others embodiments of the disclosure provided herein.

FIG. 5 depicts an alternate exemplary schematic of an exemplary optical front end 500, in accordance with others embodiments of the disclosure provided herein. Optical front end 500 comprises bias amp 520, single-ended photodiode 530, successive approximation register logic 580, IDAC 540, feedback resister 550, transimpedance amplifier (TIA) 555, buffer stage 560, analog to digital converter 570, comparator 585, and reference voltage supply 545.

In practice, the optical front end 500 has a single-ended photo-diode 530 connected to the TIA 545 input. TIA 545 performs as a current to voltage converters which are used with sensors that have a current response that is more linear than the voltage response. This is the case with photodiodes where it is not uncommon for the current response to have better than 1% nonlinearity over a wide range of light input. The transimpedance amplifier presents a low impedance to the photodiode and isolates it from the output voltage of the operational amplifier.

In its simplest form of the present embodiment, the transimpedance amplifier 545 has just a large valued feedback resistor 550, Rf. The gain of the amplifier is set by this resistor and because the amplifier is in an inverting configuration, has a value of –Rf. Other configurations of transimpedance amplifiers which convert the low-level current of a sensor to a voltage are not beyond the scope of the present disclosure.

The TIA 545 is followed by a buffer stage 560 to generate the differential outputs and then drive the ADC 570. As previously described, the photo-diode 530 current will include the reflected light off an object and the ambient light from the environment. The ambient light will cause interference to the reflected signal and even saturate the TIA 545 output when it is larger than the TIA 545 linear range.

In one or more embodiments, the photo-diode (PD) 530 is reverse biased by amp 520 with its cathode connected to the VC node and with its anode connected to the TIA 555 input, such that the PD 530 current Ipd is always in one direction. As is known in the art, increasing the reverse bias producing greater sensor sensitivity, however at the risk of pushing the TIA 555 out of its linear region and possibly into saturation.

A current DAC (IDAC) 540 circuit is added at the TIA 545 input to cancel the ambient light, such that the TIA input current only contains the compensated light signal and will maintain good signal quality. An automatic ambient cancellation loop including a coarse loop and a fine loop will control the IDAC 540 output. The coarse loop will compare the TIA 545 outputs against the threshold to set the initial DAC control code. The fine loop will use the ADC 570 sample to refresh the DAC control code. This and the functionality with respect to refresh logic 575, successive approximation register logic 580, and comparator 585 will now be discussed in greater detail with reference to FIG. 6.

Figure 6:
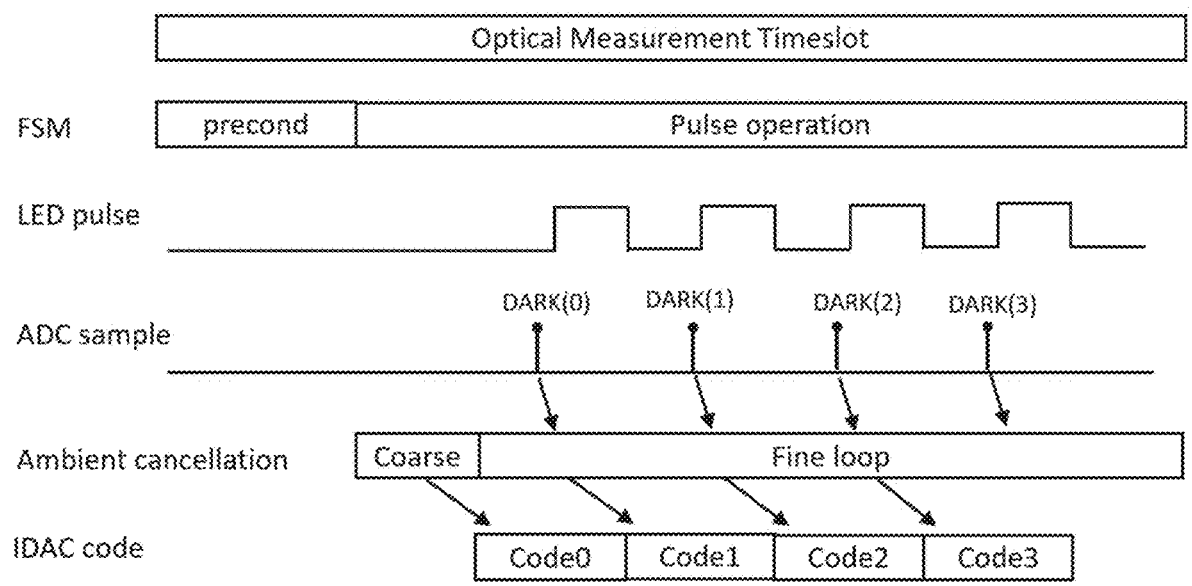
FIG. 6 demonstrates an exemplary timing diagram used to control feedback in an optical front end, in accordance with others embodiments of the disclosure provided herein.

FIG. 6 demonstrates an exemplary timing diagram used to control feedback in an optical front end, in accordance with others embodiments of the disclosure provided herein. A finite state machine (FSM) is used to set a state of precondition before switching to pulse operation, in one or more embodiments. A finite-state machine (FSM) or finite-state automaton (FSA), finite automaton, or simply a state machine, is a mathematical model of computation.

An FSM is an abstract machine that can be in exactly one of a finite number of states at any given time. The FSM can change from one state to another in response to some inputs; the change from one state to another is called a transition. An FSM is defined by a list of its states, its initial state, and the inputs that trigger each transition. Finite-state machines are of two types—deterministic finite-state machines and non-deterministic finite-state machines. A deterministic finite-state machine can be constructed equivalent to any non-deterministic one.

The finite-state machine has less computational power than some other models of computation such as the Turing machine. The computational power distinction means there are computational tasks that a Turing machine can do but an FSM cannot. This is because an FSM's memory is limited by the number of states it has. A finite-state machine has the same computational power as a Turing machine that is restricted such that its head may only perform "read" operations, and always has to move from left to right.

In operation at the beginning of the timeslot, the coarse feedback loop commences by comparing the TIA 555 output against a threshold at the comparator 585. This is performed in the dark, i.e., before the LED is illuminated. In electronics, a comparator is a device that compares two voltages or currents and outputs a digital signal indicating which is larger. It has two analog input terminals V+ and V−. The coarse loop uses a comparator to know if the TIA 555 output is in suitable range or not, so the TIA 555 gain can be maintained during the whole measurement timeslot. This has the benefit of lower power consumption and reduced delay time.

Initially, SAR logic 580 needs a logic input to tell if the DAC current is larger than the ambient or not. This input must be a binary logic signal, which comes from the comparator 585. The comparator 585 compares two analog voltage and output a binary logic. Subsequently SAR logic 580 and refresh logic 575 control IDAC 540 to produce a current corresponding to Code(0). Code(0) is the initial coarse cancellation current. Latching the IDAC 540 current to control code Code(0) ensures TIA 555 is in sufficient range (e.g., linear) to make subsequent measurement.

As can be appreciated by the timing diagram of FIG. 6, fine feedback loop commences with IDAC in a Code(0) state. Prior to LED pulsing (or between pulses), ADC 570 samples the voltage output of TIA 555. The result is an estimate of DARK(0) state. The fine feedback progresses in a corresponding manner as follows. It is noted that refresh logic 575 is usually only active during the fine loop, because it is used to refresh the DAC code when the fine loop control gets the new DARK sample. The SAR logic 580 control to the IDAC 540 during coarse loop should bypass the refresh logic 575 and go to the DAC directly. But the initial DAC code Code(0) should be remembered by the refresh logic as its starting point.

Fine feedback loop continues with IDAC in a Code(1) current state which is calculated by adding states Code(0) with DARK(0). Between pulses, ADC 570 again samples the voltage output of TIA 555. This is the result of an estimate of DARK(1) state. Fine feedback loop continues with IDAC in a Code(2) current state which is calculated by adding states Code(1) with DARK(1). Between pulses, ADC 570 again samples the voltage output of TIA 555. This is the result of an estimate of DARK(2) state. Again, the fine feedback progresses in a corresponding manner as follows.

Fine feedback loop continues with IDAC in a Code(3) current state which is calculated by adding states Code(2) with DARK(2). Between pulses, ADC 570 again samples the voltage output of TIA 555. This is the result of an estimate of DARK(3) state. While the current embodiment employs four Code and DARK states, more or less are not beyond the scope of the present disclosure.

To summarize, ADC DARK samples are used to refresh the DAC control code(s). Specifically, the previous DARK sample are used to estimate the DARK value in current period. Analytically, refresh logic 575 computationally produces:

$$Code(N)=Code(N-1)+DARK(N-1)$$

Figure 7:
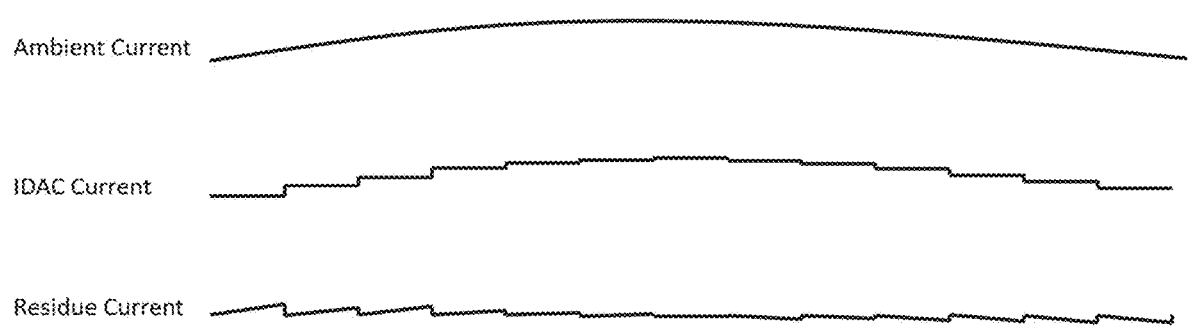
FIG. 7 demonstrates exemplary waveforms resulting from control feedback in an optical front end, in accordance with others embodiments of the disclosure provided herein.

FIG. 7 demonstrates exemplary waveforms resulting from control feedback in an optical front end, in accordance with others embodiments of the disclosure provided herein. Ambient current represents the signal received from the reversed biased photodetector. IDAC current is produced from instruction digital coding. For example, each step represents the closed loop functionality and application of feedback. The result is the residue current, which is the addition of the instruction ambient current with the IDAC current. Similar to the operation of an SAR with residuals, one skilled in the art can appreciate progressive degeneration of the residue current, which is an object of the current disclosure.

The fine loop will use the previous ADC DARK sample to know the value of ambient signal to refresh the DAC code after each LED pulse repeat, so this technique can track well with fast-moving ambient signal. The fine loop has small latency. The latency is determined by the LED pulse width and pulse repeat period.

FIGS. 8-11 illustrate different applications for sensor systems of the foregoing embodiments.

Figure 8:
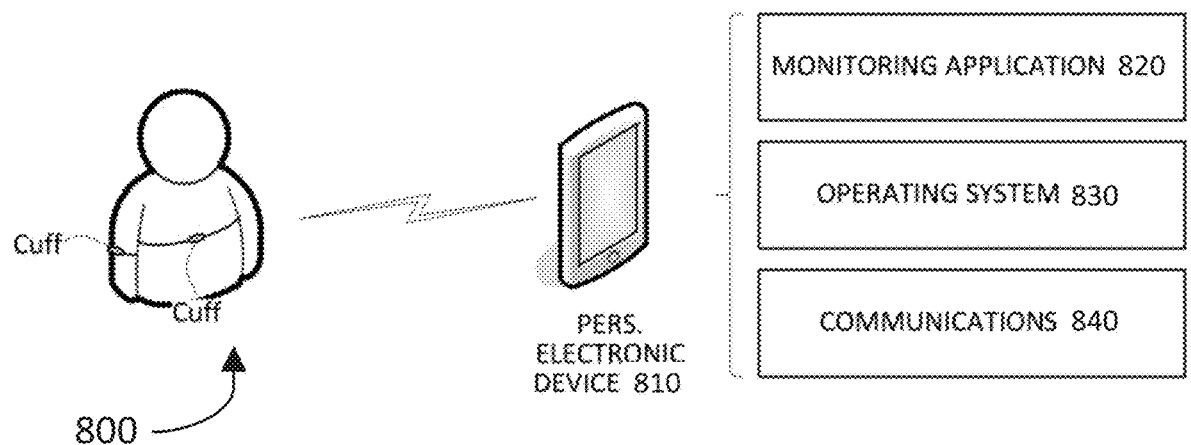
FIG. 8 depicts another exemplary wearable vital sign monitor (VSM), in accordance with some embodiments of the disclosure provided herein.

FIG. 8 depicts another exemplary wearable vital sign monitor (VSM), in accordance with some embodiments of the disclosure provided herein. In the embodiment illustrated in FIG. 8, for example, the sensor system with cancelation may be integrated into a cuff 800 that may be worn about some portion of a subject's body.

Cuffs are illustrated as provided about the arm or the chest of a subject. Alternatively, they may be integrated into headphones that place sensors in contact with the ears, into headbands that may place the sensors in contact with skin about the forehead, into wristbands, etc. The sensors may communicate with a personal electronic device 810 via wireless communications transceivers such as Bluetooth.

The personal electronic device 810 may include a monitoring application 820 to analyze signals reported to it by the sensors. The monitoring application 820 may interface with an operating system 830 and communication devices 840 within the electronic device 810 to perform its operations.

The personal electronic device 810 may be provided as a smartphone, tablet computer, personal heartrate monitor or other electronic device that collects physiological data regarding the subject. The PPG sensor systems discussed herein may be integrated with other fitness sensors that gather physiological data through other means.

Figure 9:
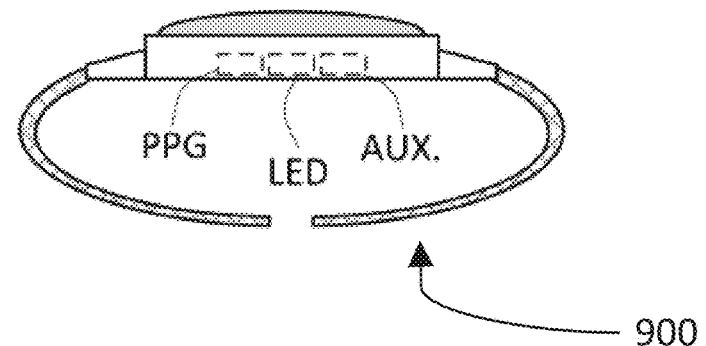
FIG. 9 depicts yet another exemplary wearable vital sign monitor (VSM), in accordance with some embodiments of the disclosure provided herein.

FIG. 9 depicts yet another exemplary wearable vital sign monitor (VSM), in accordance with some embodiments of the disclosure provided herein.

In the embodiment illustrated in FIG. 9, the sensor systems may be integrated into a wristwatch 900 or other personal accessory that is worn on a subject's body in contact with some portion of the subject's tissue. In addition to sensors, the accessory may include processors to perform analytics of the signals generated by the sensors and to derive PPG data. The wristwatch may have a display and associated controls that may display derived PPG data on command.

Figure 10:
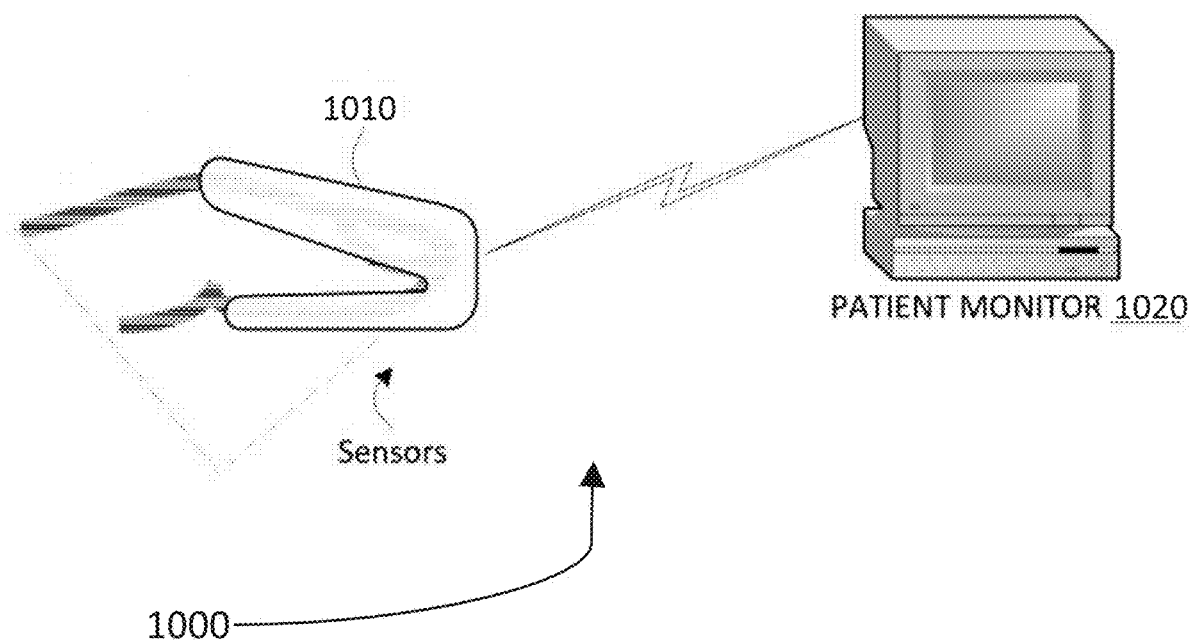
FIG. 10 depicts an exemplary finger cuff and vital sign monitoring (VSM) system, in accordance with some embodiments of the disclosure provided herein.

FIG. 10 depicts an exemplary finger cuff and vital sign monitoring (VSM) system, in accordance with some embodiments of the disclosure provided herein. FIG. 10 illustrates application of the sensor systems in a medical environment. In this embodiment, the sensors may be integrated into a sheath 1010 that is affixed to some portion of a patient's tissues (in this example, the patient's finger). The sensors may generate signals that are reported to monitoring equipment 1020 by wire-line or wireless communication link. The patient monitor 1020 may include analytics to derive physiological data from the signals reported to it by the sensors. The patient monitor 1020 also may support other types of sensors (not shown) and may generate other analytics therefrom.

While simple embodiments use pulses are used in object detection. However, any suitable waveform is not beyond the scope of the present disclosure, such as, sine wave, square-wave, sawtooth, ramp, pulse train, triangle, etc. These waveforms can be either repetitive or single-shot such as provided by an internal or external trigger source like that provided by the FSM. In fact, no AC is necessary for calibration pursuant to the present disclosure.

However, one skilled in the art will recognize the utility of a pulse sequence repeated several times to perform sampling accumulation which yields better signal quality, because the noise will be averaged by sampling accumulation. However, the ambient will change over time, so it is better to sample the ambient just before each LED pulse and refresh the DAC control for each pulse sequence. In this way, the latency between the ambient sampling and ambient cancellation is small.

In some embodiments, one or more optical filters are chosen to match the light source. For example, if a midwave infrared (MWIR) LED is used as a light source, a dichroic filter centered between 3-5 μm could be placed over the photodetector. A dichroic filter, thin-film filter, or interference filter is a very accurate color filter used to selectively pass light of a small range of colors while reflecting other colors. By comparison, dichroic mirrors and dichroic reflectors tend to be characterized by the color(s) of light that they reflect, rather than the color(s) they pass.

While dichroic filters are used in the present embodiment, other optical filters are not beyond the scope of the present invention, such as, interference, absorption, diffraction, grating, Fabry-Perot, etc. An interference filter consists of multiple thin layers of dielectric material having different refractive indices. There also may be metallic layers. In its broadest meaning, interference filters comprise also etalons that could be implemented as tunable interference filters. Interference filters are wavelength-selective by virtue of the interference effects that take place between the incident and reflected waves at the thin-film boundaries. In other embodiments, a color wheel with an optical chopper can be used as a filter.

In some embodiments a collimating lens can be used to help direct light from the light source to the object and/or focus incident light to the filter. In optics, a collimator may consist of a curved mirror or lens with some type of light source and/or an image at its focus. This can be used to replicate a target focused at infinity with little or no parallax.

The purpose of the collimating lens is to direct the light rays in coaxial light path toward the photodetector.

In one or more embodiments, the light source is an infrared light emitting diode (LED), such as, Short Wavelength Infrared (SWIR), Medium Wavelength Infrared (MWIR), and Long Wavelength Infrared (LWIR). However, other embodiments can have light emitting diodes having shorter wavelengths, such as that in the visible or ultraviolet regime. In yet other embodiments, a plurality of multiple wavelengths can be used. Any suitable, compact light producing device is not beyond the scope of the present disclosure-whether, broadband lamps, coherent, incandescent, incoherent bulb, lasers, or even thermal black-body radiation, etc.

In some embodiments, photodetectors are used as transducers to sense the light, both background and produced. Photodetectors are sensors of light or other electromagnetic energy. Photodetectors have p-n junctions that converts light photons into current. The absorbed photons make electron-hole pairs in the depletion region, which is used to detect received light intensity. In some embodiments, photodetector are photodiodes or phototransistors. However, any light detecting means, e.g., avalanche, photo-multiplier tube, etc. is not beyond the scope of the present disclosure.

SELECT EXAMPLES

Example 1 provides an optical front end for mitigating signals from ambient light comprising a differential amplifier having a first input and a second input and an output, a photodetector in electrical communication with the first input of the differential amplifier, a current source in electrical communication with the first input of the differential amplifier, and a voltage source in electrical communication with the second input of the differential amplifier, wherein the current source is configured to produce current which is substantially equal and opposite to a current produced by the photodetector.

Example 2 provides for the optical front end according to any of the preceding and/or proceeding examples further comprising a buffer amplifier having an input and output, the input in electrical communication with the output of the differential amplifier.

Example 3 provides for the optical front end according to any of the preceding and/or proceeding examples further comprising an analog to digital converter (ADC) configured to sample the output of the buffer amplifier.

Example 4 provides for the optical front end according to any of the preceding and/or proceeding examples further comprising logic configured to control a current produced by the current source.

Example 5 provides for the optical front end according to any of the preceding and/or proceeding examples, wherein the current is based on at least on the sample from the ADC.

Example 6 provides for the optical front end according to any of the preceding and/or proceeding examples further comprising a comparator.

Example 7 provides for the optical front end according to any of the preceding and/or proceeding examples further comprising a successive approximation register (SAR).

Example 8 provides for the optical front end according to any of the preceding and/or proceeding examples, wherein the current source is a current digital to analog converter (IDAC).

Example 10 provides for the optical front end according to any of the preceding and/or proceeding examples, wherein the logic to control the current is based on information from at least one of IDAC, SAR and comparator.

Example 11 provides for the optical front end according to any of the preceding and/or proceeding examples further comprising a feedback resistor in electrical communication with the input and output of the difference amplifier.

Example 12 provides for the optical front end according to any of the preceding and/or proceeding examples, wherein the differential amplifier is a transimpedance amplifier (TIA).

Example 13 provides for the optical front end according to any of the preceding and/or proceeding examples further comprising a voltage source to reverse bias the photodetector.

Example 14 provides for the optical front end according to any of the preceding and/or proceeding examples, wherein the photodetector is a single-ended photodiode.

Example 14 provides a method for mitigating signals from ambient light comprising receiving a first current from a sensor indicative of a measured light, producing a first voltage by passing the first current through a feedback resistor, comparing, at a differential amplifier having an output, the first voltage with a reference voltage, producing a second current from a current source, and canceling at least some of the first current using the second current, wherein the current source is configured to produce the second current which is substantially equal and opposite to a current produced by the sensor.

Example 15 provides for a method for mitigating signals from ambient light according to any of the preceding and/or proceeding examples further comprising comparing, at a comparator, whether the output of the differential output is above a predetermine threshold.

Example 16 provides for a method for mitigating signals from ambient light according to any of the preceding and/or proceeding examples further comprising sampling the output of the differential amplifier.

Example 17 provides for a method for mitigating signals from ambient light according to any of the preceding and/or proceeding examples, wherein the sampling is performed by an analog to digital converter (ADC).

Example 18 provides for a method for mitigating signals from ambient light according to any of the preceding and/or proceeding examples further comprising controller the current source using the sampled output, at least in part.

Example 19 provides for a method for mitigating signals from ambient light according to any of the preceding and/or proceeding examples, wherein the current source is an IDAC.

Example 20 provides for an apparatus for mitigating signals from ambient light comprising means for receiving a first current from a sensor indicative of a measured light, means for producing a first voltage by passing the first current through a feedback resistor, means for comparing, at a differential amplifier having an output, the first voltage with a reference voltage, means for producing a second current from a current source, and means for canceling at least some of the first current using the second current.

Numerous specific details have been set forth herein to provide a thorough understanding of the embodiments. It will be understood by those skilled in the art, however, that the embodiments may be practiced without these specific details. In other instances, well-known operations, components and circuits have not been described in detail so as not to obscure the embodiments. It can be appreciated that the specific structural and functional details disclosed herein may be representative and do not necessarily limit the scope of the embodiments.

The above description of illustrated embodiments, including what is described in the Abstract, is not intended to be exhaustive or limiting as to the precise forms disclosed. While specific implementations of, and examples for, various embodiments or concepts are described herein for illustrative purposes, various equivalent modifications may be possible, as those skilled in the relevant art will recognize. These modifications may be made in light of the above detailed description, the Abstract, the Figures, or the claims.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Note that the activities discussed above with reference to the FIGURES which are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe.

Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In some embodiments, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc.

Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure.

In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

INTERPRETATION OF TERMS

All definitions, as defined and used herein, should be understood to control over dictionary definitions, definitions in documents incorporated by reference, and/or ordinary meanings of the defined terms. Unless the context clearly requires otherwise, throughout the description and the claims:
  "comprise," "comprising," and the like are to be construed in an inclusive sense, as opposed to an exclusive or exhaustive sense; that is to say, in the sense of "including, but not limited to".
  "connected," "coupled," or any variant thereof, means any connection or coupling, either direct or indirect, between two or more elements; the coupling or connection between the elements can be physical, logical, or a combination thereof.
  "herein," "above," "below," and words of similar import, when used to describe this specification shall refer to this specification as a whole and not to any particular portions of this specification.
  "or," in reference to a list of two or more items, covers all of the following interpretations of the word: any of the items in the list, all of the items in the list, and any combination of the items in the list.
  the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. An optical front end for mitigating signals from ambient light comprising:
   a differential amplifier having a first input and a second input and an output;
   a photodetector in electrical communication with the first input of the differential amplifier;
   a current digital to analog converter in electrical communication with the first input of the differential amplifier; and
   a voltage source in electrical communication with the second input of the differential amplifier;
   wherein the current digital to analog converter is configured to produce a compensation current which is substantially equal and opposite to a current produced by the photodetector, and
   wherein the compensation current is determined based at least on a previous sampling of the output of the differential amplifier in a dark state and a previous compensation current.

2. The optical front end of claim 1 further comprising a buffer amplifier having an input and output, the input in electrical communication with the output of the differential amplifier.

3. The optical front end of claim 2 further comprising an analog to digital converter (ADC) configured to obtain a sample the output of the buffer amplifier.

4. The optical front end of claim 3 further comprising logic configured to control the current produced by the current digital to analog converter.

5. The optical front end of claim 4, wherein the current is based on at least on the sample from the ADC.

6. The optical front end of claim 4 further comprising a comparator.

7. The optical front end of claim 6 further comprising a successive approximation register (SAR).

8. The optical front end of claim 1, further comprising logic to control the current based on information from at least one of the current digital to analog converter (IDAC), a successive approximation register (SAR), or a comparator.

9. The optical front end of claim 1 further comprising a feedback resistor in electrical communication with the first input and output of the differential amplifier.

10. The optical front end of claim 9, wherein the differential amplifier is a transimpedance amplifier (TIA).

11. The optical front end of claim 1 further comprising a second voltage source to reverse bias the photodetector.

12. The optical front end of claim 11 wherein the photodetector is a single-ended photodiode.

13. A method for mitigating signals from ambient light comprising:
    receiving a first current from a sensor indicative of a measured light;
    producing a first voltage by passing the first current through a feedback resistor;
    comparing, at a differential amplifier having an output, the first voltage with a reference voltage;
    producing a second current from a current digital to analog converter; and
    canceling at least some of the first current using the second current;
    wherein the second current is substantially equal and opposite to the first current produced by the sensor, and
    wherein the second current is determined based at least on a previous sampling of the output of the differential amplifier in a dark state and a previous compensation current.

14. The method of claim 13 further comprising comparing, at a comparator, whether the output of the differential amplifier is above a predetermined threshold.

15. The method of claim 14 further comprising obtaining a sample of the output of the differential amplifier to be used by a future compensation of the current digital to analog converter.

16. The method of claim 15, wherein obtaining the sample of the output of the differential amplifier is performed by an analog to digital converter (ADC).

17. The method of claim 15 further comprising controlling the current analog to digital converter using the sample of the output of the differential amplifier, at least in part.

18. The method of claim 13, wherein the current digital to analog converter is programmable.

19. An apparatus for mitigating signals from ambient light comprising:
    means for receiving a first current from a sensor indicative of a measured light;
    means for producing a first voltage from the first current;
    means for comparing the first voltage with a reference voltage to produce an output;
    means for producing a second current;
    means for canceling at least some of the first current using the second current based at least on a previous sampling of the output in a dark state; and
    means for determining the second current based at least on the previous sampling of the output in the dark state and a previous compensation current, and
    wherein the second current is substantially equal and opposite to the first current.

* * * * *